United States Patent [19]
Dimitri

[11] Patent Number: 5,980,483
[45] Date of Patent: *Nov. 9, 1999

[54] DRAINAGE CATHETER FOR CONTINENT URINARY NEO-BLADDERS

[76] Inventor: Mauro Dimitri, 141, Via Delle Gondole, Rome, Italy, 00121

[ * ] Notice: This patent issued on a continued prosecution application filed under 37 CFR 1.53(d), and is subject to the twenty year patent term provisions of 35 U.S.C. 154(a)(2).

[21] Appl. No.: 08/651,947

[22] Filed: May 21, 1996

[51] Int. Cl.[6] ................................................. A61M 29/00
[52] U.S. Cl. ............................................... 604/96; 604/54
[58] Field of Search ............................. 604/54, 96–101, 604/280; 606/191, 194

[56] References Cited

U.S. PATENT DOCUMENTS

| | | | |
|---|---|---|---|
| 2,892,458 | 6/1959 | Auzin | 604/96 |
| 3,902,492 | 9/1975 | Greenhalgh | 604/96 |
| 3,905,361 | 9/1975 | Hewson et al. | 604/96 |
| 3,993,080 | 11/1976 | Loseff . | |
| 4,211,233 | 7/1980 | Lin | 604/96 |
| 4,642,092 | 2/1987 | Moss | 604/96 |
| 5,616,126 | 4/1997 | Malekmehr et al. | 604/96 |

FOREIGN PATENT DOCUMENTS

| | | |
|---|---|---|
| 381042 | 8/1990 | European Pat. Off. . |
| 471429 | 2/1992 | European Pat. Off. . |
| 483941 | 5/1992 | European Pat. Off. . |
| 2123300 | 2/1984 | United Kingdom . |

OTHER PUBLICATIONS

V. Lent, *Einroll–Ballon–Silikonkatheter zur suprapubischen Harnblasendrainage,* Urologe (B) © Springer–Verlag 1986, vol. 26, pp. 186–188.

*Primary Examiner*—Michael Buiz
*Assistant Examiner*—William Lewis
*Attorney, Agent, or Firm*—Finnegan, Henderson, Farabow, Garrett & Dunner, L.L.P.

[57] ABSTRACT

The drainage catheter for continent urinary neo-bladders, is specific in all the cases to the reconstruction of the urinary bladder either when a tract of the intestine, or when a portion of the stomach is utilized after the surgical removal of the natural bladder. The catheter can be utilized either for orthotopic urinary neo-bladders (anastomosis to the urethra), or for neo-bladders with a stoma (anastomosis to the abdominal wall), and also in enlargement entero-cystoplasties, when the natural urinary bladder is enlarged utilizing different intestinal segments. The catheter is characterized by a wide draining surface for urine, having several holes, which plays a role in preventing dangerous inadvertent obstructions of neo-bladders in the post-operatory period, caused by the continuous formation of mucous clots, when the intestine has been utilized. This catheter also prevents and minimizes bleeding caused by acid secretions when a portion of the stomach has been utilized. The catheter of the invention because of its material, its particular tip, its configuration changes the traditional approach to the patient, improving his quality of life.

25 Claims, 1 Drawing Sheet

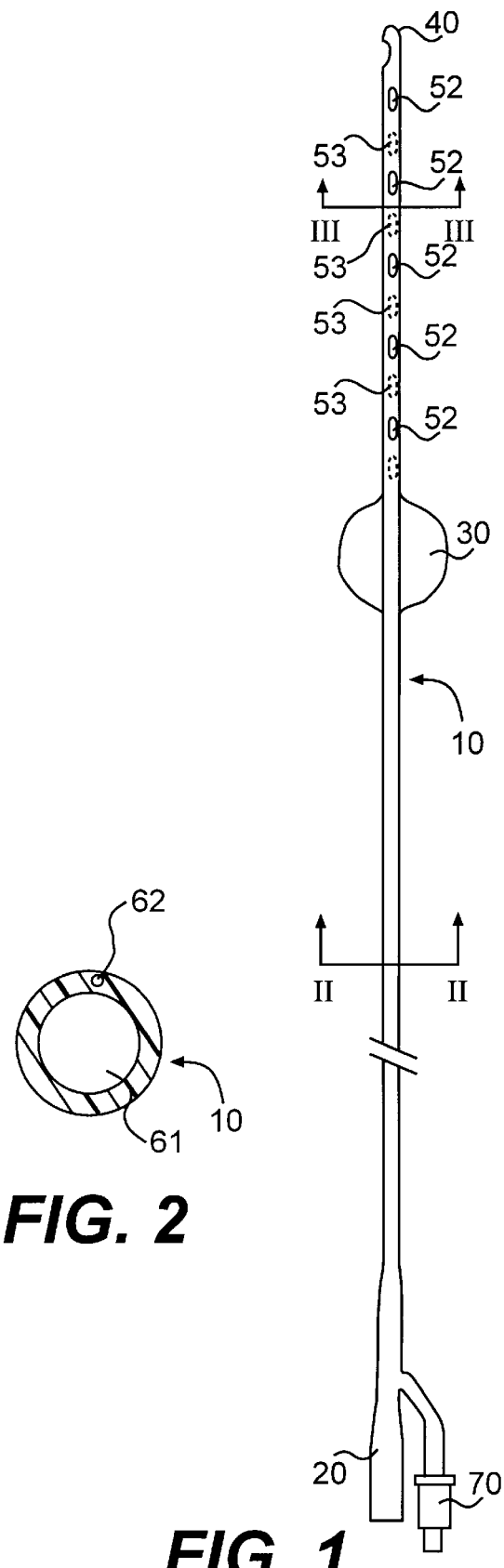
FIG. 1
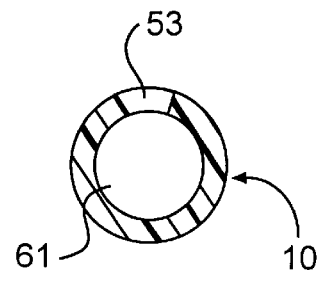
FIG. 3
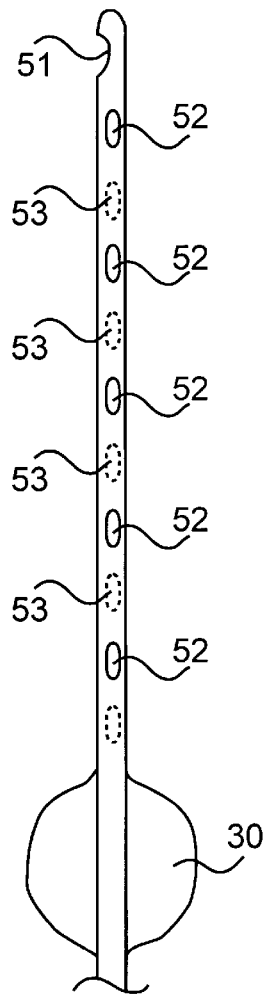
FIG. 4
FIG. 2

DRAINAGE CATHETER FOR CONTINENT URINARY NEO-BLADDERS

BACKGROUND OF THE INVENTION

Quite often, there is a need in clinical practice to remove the urinary bladder in men, women, and children, because of tumors, infections, neurologic abnormalities, or malformations. Bladder trauma is also very common after a car crash, a working accident, etc., and may require a cystectomy. Reconstruction of a new urinary bladder is common in urologic practice utilizing different segments of the intestine or of the stomach.

Two fundamental types of urinary neo-bladders allow patients to achieve urinary continence: the orthotopic neo-bladders where a patient voids through the penis, helping himself with the contraction of the abdominal musculature, and, as under normal conditions, continence is achieved with the natural sphincter; and neo-bladders with a stoma in which the neo-bladder, fashioned with a continence mechanism, communicates with the abdominal wall, and the patient catheterizes himself through the stoma to void regularly.

Common post-operatory catheters utilized for the drainage of neo-bladders are the same bladder catheters in use for many years to drain the natural bladder for the elderly, surgery of the prostate, endoscopic or partial surgery of the bladder, etc. A bladder (urethral) catheter is usually made of different materials (latex rubber, polyvinyl, polyurethane, co-polymer, silicone rubber, etc.), in different shapes and dimensions. These types of catheters are in wide use all over the world and do not show particular, technical difficulties. The balloon that anchors the catheter is made of the same rubber-elastic material in different sizes and volumes, depending on final requirements, and can be inflated or deflated through a continent valve inserted tangential to the funnel of the catheter; the balloon can be fused to the catheter or simply fixed on it, depending on the technique.

The tip of a bladder catheter is very short, about 3 cm.

Using the intestine in reconstructing the bladder, the intestinal mucosa frequently causes obstructions of the catheter by producing mucous secretions and mucous clots, with the risk of dangerous passive over distensions of the neo-bladder. The nurse personnel and the doctors must frequently wash the neo-bladders through the catheter during the two weeks of post-operatory period.

It is usually not possible to maintain a continuous washing flow through the catheter in the post-operatory period, because sudden and inadvertent obstructions not recognized immediately by the medical and nursing staff, could cause a dangerous over distension of the newly fashioned bladder and a possible rupture. Moreover, when a portion of the stomach has been utilized in reconstructing the bladder, a particular surgical procedure suitable for children, the mucosa of the portion of the stomach, utilized in the reconstruction, produces chloric acid, digestive enzymes, and mucous.

Medical therapy adequately cannot prevent the secretion of chloric acid that is sometimes responsible for severe bleeding from the mucosa (gastric) of neo-bladders. This is a common complaint for a few months after the neo-bladder procedure.

SUMMARY OF THE INVENTION

The specific drainage catheter for neo-bladders of the invention, is employed both for orthotopic neo-bladders and neo-bladders with stoma, either one utilizes the intestine or the stomach. Moreover, this specific catheter for neo-bladders can be utilizing to prevent mucous obstruction when an enlargement cystoplasty of the natural bladder is performed with a segment of the intestine. This is achieved by the particular length of the tip, and by a different positioning of the balloon from the apex of the catheter.

Moreover, the catheter is characterized by several holes along the tip of the catheter that allow a large surface for drainage; the catheter material protects it from mucous incrustation and acid secretions of the stomach.

Finally, because of the specific design and the characteristics it is possible to wash and irrigate through the neo-bladder with extreme efficacy, removing the eventual mucous clots. Bladder catheters commonly in use have a very short tip, measured from the distal end of the balloon to the apex of the catheter.

The catheter, intended especially for urinary neo-bladders, has a very long functioning tip, containing several holes to drain the urine and the mucous secretions produced by the mucosa of the intestine utilized in reconstructing the new bladder.

The holes along the common bladder catheters are usually only three. The catheter of the invention has several holes regularly placed along the two opposite sides of the tip in alternate fashion with the same diameter and distance one to each other side to side. A bigger hole is positioned at the apex of the tip.

BRIEF DESCRIPTION OF THE DRAWINGS

FIG. 1 is an elevational view of the catheter of the invention with a portion of the total length broken away.

FIG. 2 is an enlarged transverse sectional view taken on line II—II in FIG. 1.

FIG. 3 is an enlarged transverse sectional view taken on line III—III in FIG. 1.

FIG. 4 is a partial enlarged view of the tip of the catheter.

DESCRIPTION OF THE PREFERRED EMBODIMENT

The specific, technical characteristics of the catheter 10 of the invention are as follows: The catheter can be fused and shaped from hydrogel coated latex rubber or with silicone rubber materials. If the catheter is made of latex rubber, it is necessary, in order to improve its resistance to incrustations and to improve a constant lubrication of the urethra for the time during which the catheter is in place, that the catheter be hydrogel coated, a technique that in commonly in use with other catheters on the market. If the catheter is made of silicone rubber, the catheter maintains its consistency and rigidity without loosing too much elasticity, and the silicone makes the catheter resistant to incrustations from mucous and from erosion by the acid secretions from the stomach, allowing the catheter to be left in place for a long time.

The following measurements refer to a catheter of 22 French, the most commonly used size in clinical urologic practice. A "French" is a common measurement unit for bladder catheters and follows the equation: 1 mm.=0.039 inches=3 French. The total length of a catheter 10 is 52 cm. Partial measurements of this total are as follows: the portion from the funnel 20 (included) to the base of the balloon 30 is 35 cm; the funnel is 4.5 cm. From the base of the balloon to the distal end of the balloon, the length is 3 cm, if the balloon is fused to the catheter. Depending on the technical modality of construction, the balloon can also be fixed to the catheter covering it for 3.5 cm while the catheter maintains the same total length reported above of 52 cm. From the distal end of the balloon to the tip 40 of the catheter the length is 14 cm.

The tip 40 of the catheter is closed at the apex and is acutely rounded.

A number of the holes are placed along the surface of the tip from the distal end of the balloon to the apex of the catheter as follows: a total of 11 holes, ten of them measure 8 mm×3 mm.; one hole 51 measures 10 mm×4 mm. Five holes 52 are positioned on the left side of the catheter. Five holes 53 are positioned on the right side of the catheter, in alternate fashion to the contralateral holes. The larger hole 51 is positioned posteriorly and superiorly at the apex of the catheter and measures 10 mm×4 mm. The distance between the opposite holes, from side to side of the catheter measures 1.6 cm.

The balloon 30 has a volume of 30 cc, is made of the same material of the catheter 10, and can be fused or fixed on it.

The catheter 10 has an external diameter (section) of 7.3 mm (equal to 22 French, a conventional measurement unit of the catheters) along the entire length of the catheter excluding the funnel portion. The catheter has two internal co-axial channels. The first channel 61 is 3.7 mm in diameter (except for the funnel portion), is shaped as a tunnel, and communicates with the two extremities of the catheter: the holes along the tip of the catheter and with the funnel portion and then the outside. The second channel 62 is positioned in the thickness of the wall of the catheter just peripheral and co-axial to the first channel and measures 0.7 mm in diameter. This thin channel communicates with a continent valve 70 and the balloon. The continent valve is implanted for fusion tangential to the catheter and placed parallel to the funnel, with the balloon. The continent valve measures 6.5 cm and generally for 22 French catheters is about 1 cm in an external diameter, depending on the type of valve already on the market.

The first channel 61 at the funnel end measures 7.5 mm and can be connected to common syringes for catheters of 60 ml or 100 ml funnel shaped in use to wash the bladder.

The catheter material is mixed with barium sulfate in such a percentage that makes the catheter visible inside the neo-bladder with conventional X-Rays. The catheter of my invention, even with large variations in sizes from children to adults (10 Fr.;12 Fr.;14 Fr.;16 Fr.;18 Fr.;20.Fr.;22 Fr.;24 Fr.), can maintain the same configuration and the same shape following this equation 1 mm=0.39 inches=3 French.

I claim:

1. A drainage catheter for continent urinary neo-bladders, comprising:
    a flexible tube having a continuous channel between a funnel end and an apex end, the apex end being closed and rounded;
    an inflatable balloon fixed on the tube;
    a tip portion of the tube having a length extending from the balloon to the apex end of the tube;
    a plurality of holes located linearly along and staggered on different sides of the tip portion, the plurality of holes being of equal size and defining passages for fluid flow alternately to and from the continuous channel throughout the length of the tip portion of the tube; and
    a single hole located adjacent the apex end of the tube, the single hole having a larger size than each of the plurality of holes and providing for fluid passage to and from the continuous channel.

2. A drainage catheter for continent urinary neo-bladders, as in claim 1, wherein each of the plurality of holes measures 8 mm×3 mm and the single hole measures 10 mm×4 mm.

3. A drainage catheter for continent urinary neo-bladders, as in claim 1, wherein the plurality of holes includes a first set of holes located linearly along the tip and a second set of holes located linearly along the tip opposite from the first set of holes, wherein the single hole is oriented differently than either of the first and second sets of holes.

4. A drainage catheter for continent urinary neo-bladders, as in claim 3, wherein the first and second plurality of holes each comprises 5 holes located linearly along the tip.

5. A drainage catheter for continent urinary neo-bladders, as in claim 1, wherein the balloon can inflate to a volume of 30 cc is fused or fixed to the tube.

6. A drainage catheter for continent urinary neo-bladders, as in claim 1, wherein the tube has a diameter between 10 French to 24 French.

7. A drainage catheter for continent urinary neo-bladders, as in claim 1, wherein the catheter has a total length of 52 cm and the tip has a length of 14 cm.

8. A drainage catheter for continent urinary neo-bladders, as in claim 1, wherein the tube is formed of hydrogel coated latex rubber.

9. A drainage catheter for continent urinary neo-bladders, as in claim 1, wherein the tube is formed of silicone rubber.

10. A drainage catheter for continent urinary neo-bladders, as in claim 1, wherein the catheter is formed of a material mixed with barium sulfate for making the catheter visible by using x-rays.

11. A method of treating a continent urinary neo-bladder, comprising the steps of:
    providing a catheter including a flexible tube having a continuous channel between a funnel end and an apex end, an inflatable balloon fixed on the tube, a tip portion of the tube having a length extending from the balloon to the apex end of the tube, a plurality of holes located linearly along and staggered on different sides of the tip portion, the plurality of holes being of equal size and defining passages for fluid flow alternately to and from the continuous channel throughout the length of the tip portion of the tube;
    inserting the tip portion and the balloon into a neo-bladder;
    inflating the balloon to hold the catheter in the neo-bladder; and
    draining urine from the neo-bladder through the holes and passages of the catheter.

12. The method of treating a continent urinary neo-bladder, as in claim 11, wherein the catheter includes a single hole at the apex end of the tube larger than each of the plurality of holes, each of the plurality of holes and the single hole providing for fluid passage to and from the continuous channel.

13. The method of treating a continent urinary neo-bladder, as in claim 12, wherein each of the plurality of holes measures 8 mm×3 mm and the single hole measures 10 mm×4 mm.

14. The method of treating a continent urinary neo-bladder, as in claim 12, wherein the plurality of holes includes a first set of holes located linearly along the tip and a second set of holes located linearly along the tip opposite from the first set of holes, wherein the single hole is oriented differently than either of the first and second sets of holes for effectively draining, washing, and irrigating the neo-bladder.

15. The method of treating a continent urinary neo-bladder, as in claim 14, wherein the first and second plurality of holes each comprises 5 holes located linearly along the tip.

16. The method of treating a continent urinary neo-bladder, as in claim 11, wherein the apex end of the tip is closed and rounded.

17. The method of treating a continent urinary neo-bladder, as in claim 11, wherein the balloon can inflate to a volume of 30 cc and is fused or fixed to the tube.

18. The method of treating a continent urinary neo-bladder, as in claim 11, wherein the tube has a diameter between 10 French to 24 French.

19. The method of treating a continent urinary neo-bladder, as in claim 11, wherein the catheter has a total length of 52 cm and the tip has a length of 14 cm to provide a large surface for effective drainage of urine and mucous secretions from the neo-bladder.

20. The method of treating a continent urinary neo-bladder, as in claim 11, wherein the tube is formed of hydrogel coated latex rubber to protect the catheter from mucous secretions and stomach acid secretions.

21. The method of treating a continent urinary neo-bladder, as in claim 11, wherein the tube is formed of silicone rubber to protect the catheter from mucous secretions and stomach acid secretions.

22. The method of treating a continent urinary neo-bladder, as in claim 11, wherein the catheter is formed of a material mixed with barium sulfate making the catheter visible using x-rays.

23. The method of treating a continent urinary neo-bladder, as in claim 11, further comprising the steps of alternately draining, irrigating, and washing the neo-bladder through the holes and passages of the catheter to remove urine and mucous secretions.

24. The method of treating a continent urinary neo-bladder, as in claim 11, wherein the neo-bladder comprises a portion of a stomach.

25. The method of treating a continent urinary neo-bladder, as in claim 11, wherein the neo-bladder comprises a portion of an intestine.

* * * * *